US007608262B2

(12) United States Patent
Elliott et al.

(10) Patent No.: US 7,608,262 B2
(45) Date of Patent: Oct. 27, 2009

(54) METHODS OF PREVENTING OR TREATING THROMBOSIS WITH TUMOR NECROSIS FACTOR ANTAGONISTS

(75) Inventors: Michael J. Elliott, London (GB); Ravinder N. Maini, London (GB); Marc Feldmann, London (GB)

(73) Assignee: The Kennedy Institute of Rheumatology, London (GB)

( * ) Notice: Subject to any disclaimer, the term of this patent is extended or adjusted under 35 U.S.C. 154(b) by 0 days.

(21) Appl. No.: 08/602,272

(22) Filed: Feb. 16, 1996

(65) Prior Publication Data

US 2002/0081306 A1    Jun. 27, 2002

(51) Int. Cl.
*A61K 39/395* (2006.01)
(52) U.S. Cl. ............... 424/141.1; 424/145.1; 424/172.1
(58) Field of Classification Search ............... 424/158.1, 424/130.1
See application file for complete search history.

(56) References Cited

U.S. PATENT DOCUMENTS

| 5,231,024 | A |   | 7/1993 | Moeller et al. ......... 435/240.27 |
| 5,317,019 | A | * | 5/1994 | Bender et al. ............ 514/224.2 |
| 5,436,154 | A | * | 7/1995 | Barbanti |
| 5,447,851 | A |   | 9/1995 | Beutler et al. .............. 435/69.7 |
| 5,547,979 | A | * | 8/1996 | Christensen |
| 5,656,272 | A | * | 8/1997 | Le et al. |
| 5,698,195 | A |   | 12/1997 | Le |
| 5,863,531 | A | * | 1/1999 | Naughton et al. .......... 424/93.7 |

FOREIGN PATENT DOCUMENTS

| EP |       260610 A3  | 3/1988 |
| EP |       453898 A2  | 10/1991 |
| EP |       486809 A2  | 5/1992 |
| EP |       626389 A1  | 11/1994 |
| GB |      2289218 A   | 11/1995 |
| WO |    WO 91/15451   | 10/1991 |
| WO |    WO 92/09203  * | 6/1992 |
| WO |       9216553  * | 10/1992 |
| WO |    WO 92/16553   | 10/1992 |
| WO |    WO 94/10990   | 5/1994 |
| WO |    WO 95/03827 A | 2/1995 |
| WO |    WO 95/19957   | 7/1995 |
| WO |    WO 96/21447   | 7/1996 |

OTHER PUBLICATIONS

Squadrito, Ev. J. Pharmocology 237: 223-230, 1993.*
Wolfe, Arthritis and Rheumatism 37(4) ;481-494, 1994.*
Meade, European Heart J 16 (Suppl A); 31-35, 1995.*
vander Poll, Blood 83 : 446 1994.*
Hommes et al, Gastroenterology, 1995, vol. 108, No. 4, suppl., p. A838.*
Leardi et al, Italian journal of surgical Sciences, 1983, vol. 13, pp. 197-201, (abstract only).*
Arii et al, Circulation, 1994, vol. 90, No. 4, pat 2, p. I 522.*
Vertrees et al, Asaio Journal, 1994, vol. 40, p. M554-M559.*
Wakefield et al, Arteriosclerosis, Thrombosis and Vascular Biology, 1995, vol. 15, pp. 258-268.*
Dhainaut et al, Critical Care Medicine, 1995, vol. 23, pp. 1461-1469. (abstract only).*
Fisher et al, Critical Care Medicine, 1993, vol. 21, pp. 318-327. (abstract only).*
Hooper et al, Blood, 1994, vol. 84, pp. 483-489.*
Clark (Protein Engineering of Antibody Molecules for Prophylactic and Therapeutic Applications in Man, 1993, p. 1).*
Wakefield et al (Arteriosclerosis, Thrombosis and Vascular Biology, 1995, vol. 15, pp. 258-268).*
Arbustini et al (American Journal of Cardiology, 1991, vol. 68,pp. B36-B50).*
The abstract of Riipi et al (Infection and Immunity, 1990, vol. 58, pp. 2750-2754).*
Handin, R. 'Disorders of Coagulation and Thrombosis', In: Harrison's Principles of Internal Medicine, 13th Ed., vol. 1, Isselbacher et al, Ed., pp. 1804-1810.*
Abstract of Martini et al (Current Therapeutic Research, 1993, vol. 53, pp. 340-346).*
Abstract of Di Perry et al (Haemostasis, 1986, vol. 16 Suppl. 1, pp. 42-47).*
Abstracts of Mozzi et al (Haemostasis, 1986, vol. 16 Suppl. 1, pp. 36-38).*
Abstract of Ciavarella et al (Haemostasis, 1986, vol. 16 Suppl. 1, pp. 39-41).*
Creager et al ('Vascular Diseases of the Extremities', In: Harrison's Principles of Internal Medicine, 13th Ed., vol. 1, Isselbacher et al, Ed., pp. 1135-1142).*
Charles et al (Journal of Immunology, 1999, vol. 163, pp. 1521-1528).*
Abstract of Squadrito et al (European Journal of Pharmacology, 1993, vol. 237, pp. 223-230).*
Abstract of Strieter et al (Critical Care Medicine, 1993, 21(10 suppl):S447-S463).*
Elliott, M. J., et al., "Treatment of Rheumatoid Arthritis with Chimeric Monoclonal Antibodies to Tumor Necrosis Factor α," *Arthritis & Rheumatism*, 36(12): 1681-1690 (1993).
Elliott, M. J., et al., "Randomised double-blind comparision of chimeric monoclonal antibody to tumour necrosis factor α (cA2) versus placebo in rheumatoid arthritis," *The Lancet*, 344: 1105-1110 (1994).
Wolfe, F., et al., "The Mortality of Rheumatoid Arthritis," *Arthritis & Rheumatism*, 37(4): 481-494 (1994).
Meade, T.W., "Fibrinogen in ischaemic heart disease," *European Heart J.*, 16(Suppl. A): 31-35 (1995).
Brown, A.S., and Martin, J.F., "The megakaryocyte platelet system and vascular disease," *European J. of Clinical Investigation*, 24 (Suppl. 1): 9-15 (1994).
Davidsen, S.K. and Summers, J.B., "Inhibitors of TNFα Synthesis," *Exp. Opin. Ther. Patents*, 5(10): 1087-1100 (1995).

(Continued)

*Primary Examiner*—Karen A Canella
(74) *Attorney, Agent, or Firm*—John P. White; Cooper & Dunham LLP

(57) ABSTRACT

A method of treating or preventing a cardiovascular and/or a cerebrovascular disorder in an individual is disclosed. Also disclosed is a method for treating and/or preventing a thrombotic disorder in an individual. Further disclosed is a method of decreasing plasma fibrinogen in an individual.

1 Claim, 4 Drawing Sheets

OTHER PUBLICATIONS

Lee, J.C. et al., "Low-Molecular-Weight TNF Biosynthesis Inhibitors: Strategies and Prospectives," *Circ. Shock* 44:97-103 (1995).

Neuner, P. et al., "Pentoxifylline in Vivo Down-Regulates the Release of IL-1β, IL-6, IL-8 and Tumour Necrosis Factor-α by Human Peripheral Blood Mononuclear Cells," *Immunology*, 83(2):262-267 (1994).

Bertini, R., et al., "Depression Of Liver Drug Metabolism And Increase In Plasma Fibrinogen By Interleukin 1 And Tumor Necrosis Factor: A Comparison With Lymphotoxin And Interferon," *Int J. Immunopharmac.* (1988), 19(5):525-530.

Bertini, R., et al., "Dexamethasone modulation of in vivo effects of endotoxin, tumor necrosis factor, and interleukin-1 on liver cytochrome P-450, plasma fibrinogen and serum iron," *J. Leukoc. Biol.* (1989), 46(3):254-62.

Gresser, I., et al., "Tumor necrosis factor induces acute phase proteins in rats," *Biol. Regul. Homeost. Agents* (1987), 1(4):173-6.

Nawroth, P., et al., "Tumor Necrosis Factor/Cachectin-Induced Intravascular Fibrin Formation In Meth A Fibrosarcomas," *J. Exp. Med.* (1988), 168:637-647.

Sekut, L., et al., "Anti-inflammatory activity of phosphodiesterase (PDE)-IV inhibitors in acute and chronic models of inflammation," *Clin. Exp. Immunol.* (1995), 100(1):126-32.

Soria, J., et al., "Pentoxifylline, fibrinogen and leukocytes," *Blood Coagul. Fibrinolysis* (1990), 1(4-5):485-7.

Van Der Poll, T., et al., "Fibrinolytic Response to Tumor Necrosis Factor in Healthy Subjects," *J. Exp. Med.* (1991), 174:729-732.

Van Hinsbergh, V.W., et al., "Progress of fibrinolysis during tumor necrosis factor infusions in humans. Concomitant increase in tissue-type plasminogen activator, plasminogen activator inhibitor type-1, and fibrin(ogen) degradation products," *Blood* (1990), 76(11):2284-9; and.

Zabel, P. et al., "Inhibition of endogenous TNF formation by pentoxifylline," *Immunobiology* (1993), 187(3-5):447-63, review.

Centocor, Inc.'s Remicade (infliximab) Products Webpage, http://www.centocor.com/cgi-in/site/products/prod_remicade.cgi (Jun. 22, 2004).

Oct. 28, 1999 Pharmacological Review for Remicade (infliximab) from the U.S. Food and Drug Administration's Center For Drug Evaluation And Research, http://www.fda.gov/cder/biologics/review/inflcen111099r2.pdf (Jun. 21, 2004).

Label and Approval History for Remicade (infliximab) from the U.S. Food and Drug Administration's Center for Evaluation And Research, http://www.accessdata.fda.gov/scripts/cder/drugsatfda/index.cfm?fuseaction=Search.Label_ApprovalHistory#apphist (Jun. 21, 2004).

\* cited by examiner

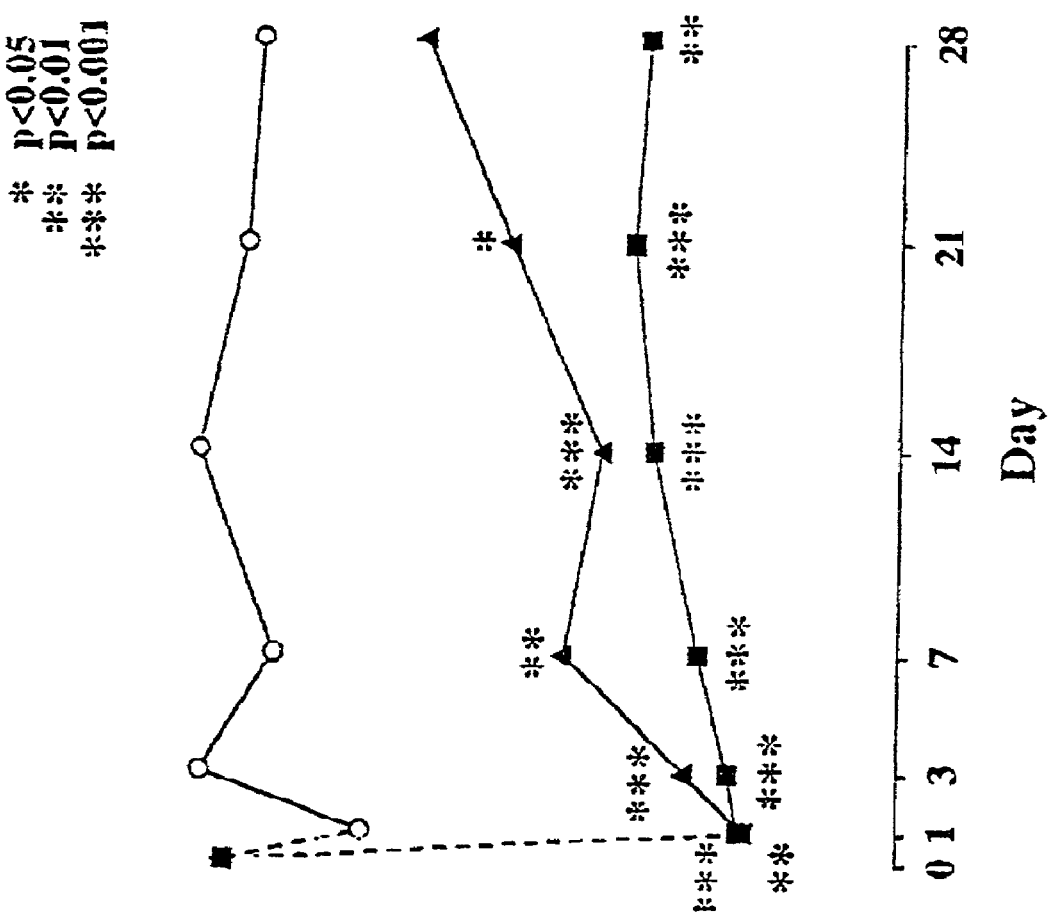
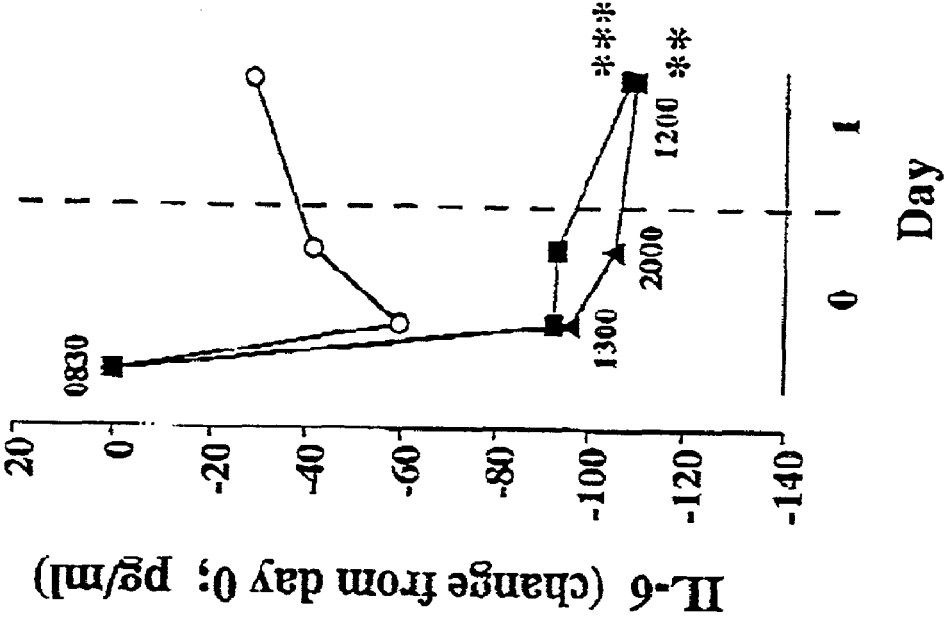
Figure 1A
Figure 1B

```
                         SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
            (A) LENGTH: 22 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:1:

Tyr Ser Gln Val Leu Phe Lys Gly Gln Gly Cys Pro Ser Thr His Val
   1               5                  10                  15

Leu Leu Thr His Thr Ile
                20

(2) INFORMATION FOR SEQ ID NO:2:

(i) SEQUENCE CHARACTERISTICS:
            (A) LENGTH: 22 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:2:

Tyr Gln Thr Lys Val Asn Leu Leu Ser Ala Ile Lys Ser Pro Cys Gln
   1               5                  10                  15

Arg Glu Thr Pro Glu Gly
                20
```

METHODS OF PREVENTING OR TREATING THROMBOSIS WITH TUMOR NECROSIS FACTOR ANTAGONISTS

BACKGROUND OF THE INVENTION

Platelets and fibrinogen play integral roles in the formation of blood clots (thrombi). Platelets first adhere to macromolecules in the subendothelial regions of an injured blood vessel; they then aggregate to form the nidus of a thrombus. Platelet aggregation is mediated by fibrinogen binding to the activated platelet membrane glycoprotein IIb/IIIa (GP IIb/IIIa) receptor. The platelets stimulate local activation of plasma coagulation factors, which leads to the conversion of fibrinogen bound to GP IIa/IIIb receptor to fibrin monomers which polymerize to form the matrix (fibrin clot) of a thrombus.

Epidemiological studies have shown that elevated levels of plasma fibrinogen are associated with acute myocardial infarction, ischemic heart disease, coronary mortality, stroke in men, deep vein thrombosis and throbophlebitis (Meade et al., *Eur. Heart J.* 16 *Suppl A:*31-35 (1995); Meade et al., *Br. Med. Bull.* 33:283-288 (1977); Meade et al., *Lancet ii:*533-537 (1986); Wilhelmsen et al., *N. Engl. J. Med.* 311:501-505 (1984); Kannel et al., *JAMA* 258:1183-1186 (1987); Stone and Thorp, *J. R. Coll. Gen. Pract.* 35:565-569 (1985); Balleisen et al., *Lancet ii:*461 (1987); Lee et al., *J. Clin. Epidemiol.* 43:913-919 (1990); Moller and Kristensen, *Arterioscler. Thromb.* 11:344-350 (1991); Broadhurst et al., *Atherosclerosis* 85:169-173 (1990); Handa et al., *Atherosclerosis* 77:209-213 (1989)).

Increased levels of platelet GP IIa/IIIb receptors are also associated with acute myocardial infarction (Brown et al., *Eur. J. Clin. Invest.* 24 *Suppl.* 1:9-15 (1994); Giles et al., *Eur. J. Clin. Invest.* 24:69-72 (1994)).

Platelets play an important role in the development of the atherosclerotic lesions that typically underlie coronary artery disease, aortic aneurysm, arterial disease of the lower extremities and cerebrovascular disease.

Thus, elevated circulating fibrinogen and/or platelet levels are independent risk factors that are at least as significant as cholesterol or hypertension for vascular diseases, such as coronary heart disease and cerebrovascular disease.

SUMMARY OF THE INVENTION

The present invention is based on the surprising discovery that inhibition of the biological activity of tumor necrosis factor α (TNFα) reduces fibrinogen and platelet levels in individuals with active rheumatoid arthritis. As a result of Applicants' discovery, a method is provided herein to treat and/or prevent a cardiovascular and/or a cerebrovascular disorder in an individual comprising administering a therapeutically effective amount of a tumor necrosis factor (TNF) antagonist to the individual.

In a second embodiment, the invention relates to a method for treating and/or preventing a thrombotic disorder in an individual comprising administering a therapeutically effective amount of a TNF antagonist to the individual.

In another embodiment, the present invention relates to a method of decreasing plasma fibrinogen in an individual comprising administering a therapeutically effective amount of a TNF antagonist to the individual.

The present invention further relates to a method of decreasing platelet levels and/or platelet aggregation in an individual comprising administering a therapeutically effective amount of a TNF antagonist to the individual.

TNF antagonists useful in the methods of the present invention include anti-TNF antibodies and receptor molecules which bind specifically to TNF, compounds which prevent and/or inhibit TNF synthesis or TNF release, such as thalidomide, phosphodiesterase inhibitors (e.g., pentoxifylline and rolipram), tenidap, A2b adenosine receptor agonists and A2b adenosine receptor enhancers and compounds which prevent and/or inhibit TNF receptor signalling.

BRIEF DESCRIPTION OF THE DRAWINGS

FIGS. 1A-1B are graphic representations of results showing the effect of TNFα on circulating interleukin-6 (IL-6). FIG. 1A shows a detailed time/response profile on day 0 and 1, with the mean sampling times indicated. FIG. 1B shows changes in circulating IL-6 in the same three patient groups over the longer term.

FIG. 4A shows the relationship between circulating IL-6 and CRP in all 73 patients pre-treatment (Spearman's rank correlation coefficient ($\rho=0.55$, $p<0.002$). FIG. 4B shows the relationship between the reduction in circulating IL-6 by day 3 and the reduction in CRP over the same period in all 73 patients ($\rho=0.59$, $p<0.002$).

DETAILED DESCRIPTION OF THE INVENTION

Figure 2:
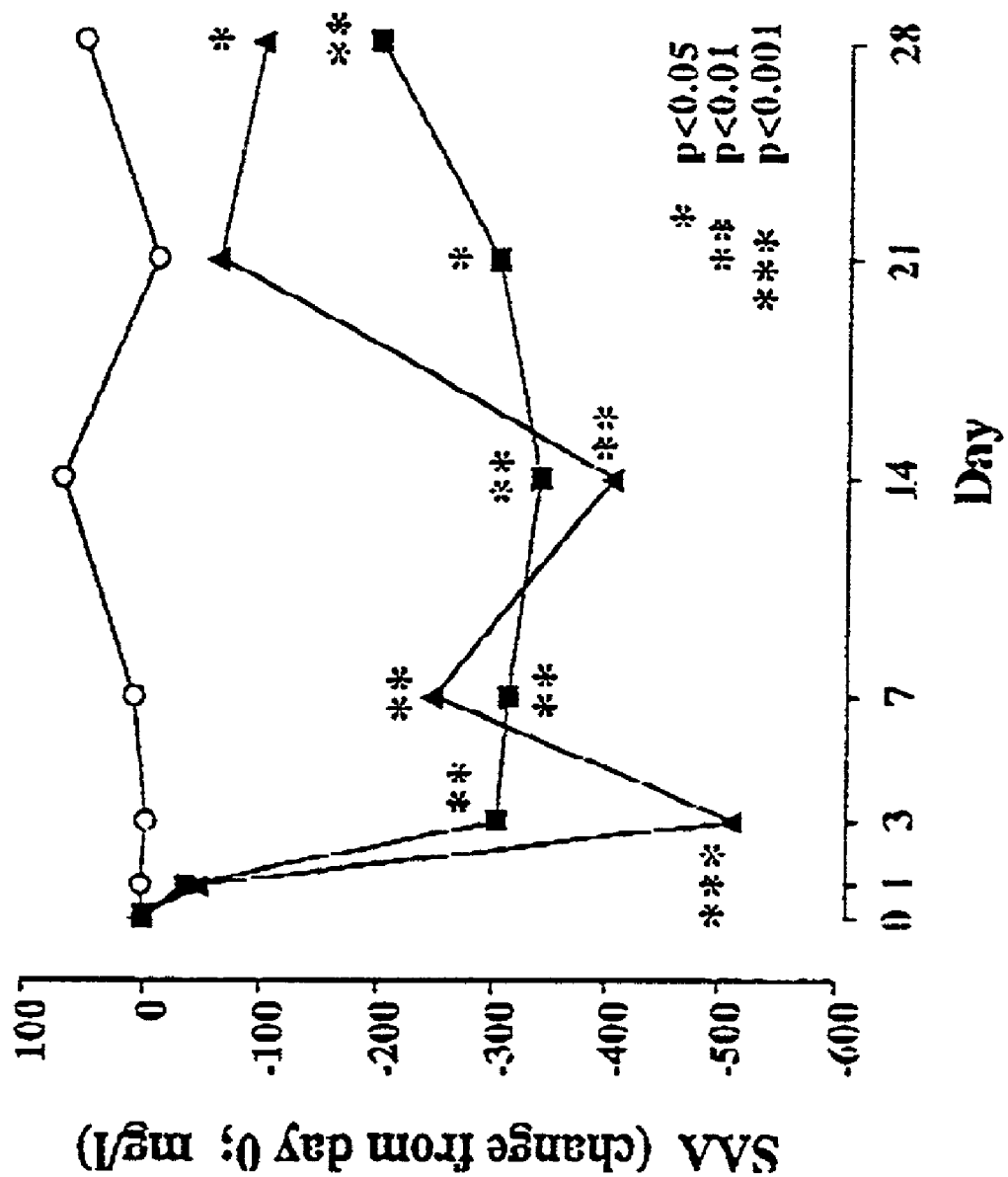
FIG. 2 is a graphic representation of results showing the effect of TNFα blockade on circulating serum amyloid A (SAA).

Many patients with rheumatoid arthritis (RA) ultimately die from cardiovascular and cerebrovascular diseases. Although other factors undoubtedly also contribute to the excess cardiovascular and cerebrovascular mortality seen in RA (Wolfe et al., *Arthritis Rheum.* 37:481-494 (1994)), persistently elevated plasma fibrinogen and/or platelet levels are major contributors to these diseases.

Platelets and fibrinogen play integral roles in the formation of blood clots (thrombi). Typically, the formation of a blood clot begins with the adhesion of platelets to macromolecules in the subendothelial regions of the injured blood vessel. The adhesion of platelets is mediated by platelet surface receptors which bind to extracellular matrix proteins in the exposed subendothelium, such as von Willebrand factor, collagen, fibronectin, vitronectin and laminin. Platelet adhesion results in a monolayer of platelets. Platelet activation subsequently occurs in response to agonists such as epinephrine, adenosine diphosphate (ADP), collagen and thrombin. Activation leads to the exposure of GP IIb/IIIa receptors on the platelet surface. GP IIb/IIIa receptors on activated platelets are then available to bind adhesive proteins, typically fibrinogen. Subsequently, platelets aggregate to form the primary hemostatic plug.

Platelet aggregation is mediated, at least in part, by the cross-linking by fibrinogen of GP IIb/IIIa receptors on adjacent platelet membranes. Fibrinogen bound to the GP IIb/IIIa receptors is cleaved by thrombin into fibrin monomers which then polymerize to form the matrix of the blood clot. Formation of the fibrin meshwork (fibrin clot) results in reinforcement and stabilization of the platelet plug at the site of vascular disruption.

Under normal circumstances, blood clots serve to prevent the escape of blood cells from the vascular system, a desirable effect upon incurring a blood vessel wound. However, during certain disease states, clots can restrict or totally occlude blood flow resulting in cellular necrosis.

The work described herein clearly shows the surprising result that TNFα blockade in the short term leads to normalisation of fibrinogen levels in many patients and suggests that fibrinogen levels can be controlled through effective long term TNF blockade. The surprising result that TNFα blockade in the short term leads to normalisation of platelet levels was described in U.S. application Ser. No. 08/324,799 (filed Oct. 18, 1994); Elliott et al., *Arthritis Rheum.* 36:1681-1690 (1993); and Elliott et al., *Lancet* 344:1105-1110 (1994), which references are entirely incorporated herein by reference.

Reducing plasma fibrinogen and platelet levels reduces the risk of developing many cardiovascular, cerebrovascular and thrombotic disorders. Thus, the development or progression of these disorders can be prevented or decreased with long term blockade of TNF. Cardiovascular, cerebrovascular and thrombotic disorders can also be treated with long term blockade of TNF.

The present invention is directed to a method for treating and/or preventing a cardiovascular and/or a cerebrovascular disorder in an individual. The method comprises administering a therapeutically effective amount of a TNF antagonist to the individual. As used herein, a "cardiovascular disorder" includes acute myocardial infarction, and cardial thrombotic disorders, such as deep vein thrombosis and thrombophlebitis. As used herein, a "cerebrovascular disorder" includes vascular disorders related to the brain, such as stroke.

The present invention is also directed to a method of treating and/or preventing a thrombotic disorder in an individual comprising administering a therapeutically effective amount of a TNF antagonist to the individual. As used herein, a "thrombotic disorder" is a condition where thrombosis is a pathogenic component. For example, a "thrombotic disorder" includes thromboembolic disorders (e.g., pulmonary thromboembolism), ischemic events (e.g., transient ischemic attack), stroke, acute myocardial infarction, deep vein thrombosis and thrombophlebitis.

The present invention further relates to a method of decreasing plasma fibrinogen in an individual comprising administering a therapeutically effective amount of a TNF antagonist to the individual. The TNF antagonist binds with high affinity to TNFα in the individual, resulting in a reduction in plasma fibrinogen in the individual. For example, as shown in the Example, administration of the antibody chimeric A2 (cA2) to 49 patients resulted in a significant reduction in plasma fibrinogen in many of the patients.

The present invention can be used to treat and/or prevent thrombosis. For example, the present invention can be used to prevent thrombosis in pulmonary embolism, ischemic events (e.g., transient ischemic attack), deep vein thrombosis, coronary bypass surgery, surgery to insert a prosthetic valve or vessel (e.g., in autologous, non-autologous or synthetic vessel graft) or deployment of a vascular (coronary or peripheral) stent. The invention can also be used to treat and/or prevent occlusion, reocclusion, stenosis and/or restenosis of blood vessels. For example, the invention can be used to treat and/or prevent reocurrence of cardiovascular, cerebrovascular and/or thrombotic disorders.

TNFα, a pleiotropic cytokine released by activated T cells and macrophages, is expressed as a mature 17 kDa protein that is active as a trimer (Smith, R. A. and Baglioni, C., *J. Biol. Chem.* 262: 6951-6954 (1987)). Trimeric cytokines such as TNFα and the closely related protein lymphotoxin (TNFβ), exert their biological activity by aggregating their cell surface receptors. The TNF trimer binds the receptors on the cell surface causing localized crosslinking of TNF receptors into clusters necessary for signal transduction. As used herein, a "tumor necrosis factor antagonist" decreases, blocks, inhibits, abrogates or interferes with TNF activity in vivo. For example, a suitable TNF antagonist can bind TNF and includes anti-TNF antibodies and receptor molecules which bind specifically to TNF. A suitable TNF antagonist can also prevent or inhibit TNF synthesis and/or TNF release and includes compounds such as thalidomide, tenidap, and phosphodiesterase inhibitors, such as, but not limited to, pentoxifylline and rolipram. A suitable TNF antagonist that can prevent or inhibit TNF synthesis and/or TNF release also includes A2b adenosine receptor enhancers and A2b adenosine receptor agonists (e.g., 5'-(N-cyclopropyl)-carboxamidoadenosine, 5'-N-ethylcarboxamidoadenosine, cyclohexyladenosine and R—$N^6$-phenyl-2-propyladenosine). See, for example, Jacobson (GB 2 289 218 A), the teachings of which are entirely incorporated herein by reference. A suitable TNF antagonist can also prevent and/or inhibit TNF receptor signalling.

Anti-TNF Antibodies

Anti-TNF antibodies useful in the methods of the present invention include monoclonal, chimeric, humanized, resurfaced and recombinant antibodies and fragments thereof which are characterized by high affinity binding to TNF and low toxicity (including human anti-murine antibody (HAMA) and/or human anti-chimeric antibody (HACA) response). In particular, an antibody where the individual components, such as the variable region, constant region and framework, individually and/or collectively possess low immunogenicity is useful in the present invention. The antibodies which can be used in the invention are characterized by their ability to treat patients for extended periods with good to excellent alleviation of symptoms and low toxicity. Low immunogenicity and/or high affinity, as well as other undefined properties, may contribute to the therapeutic results achieved.

An example of a high affinity monoclonal antibody useful in the methods of the present invention is murine monoclonal antibody (mAb) A2 and antibodies which will competitively inhibit in vivo the binding to human TNFα of anti-TNFα murine mAb A2 or an antibody having substantially the same specific binding characteristics, as well as fragments and regions thereof. Murine monoclonal antibody A2 and chimeric derivatives thereof are described in U.S. application Ser. No. 08/192,093 (filed Feb. 4, 1994, now U.S. Pat. No. 5,919,452), U.S. application Ser. No. 08/192,102 (filed Feb. 4, 1994, now U.S. Pat. No. 5,656,272), U.S. application Ser. No. 08/192,861 (filed Feb. 4, U.S. application Ser. No. 08/324,799 (filed Oct. 18, 1994 now U.S. Pat. No. 5,698,195, and Le, J. et al., International Publication No. WO 92/16553 (published Oct. 1, 1992), which references are entirely incorporated herein by reference. A second example of a high affinity monoclonal antibody useful in the methods of the present invention is murine mAb 195 and antibodies which will competitively inhibit in vivo the binding to human TNFα of anti-TNFα murine 195 or an antibody having substantially the same specific binding characteristics, as well as fragments and regions thereof. Other high affinity monoclonal antibodies useful in the methods of the present invention include murine mAb 114 and murine mAb 199 and antibodies which will competitively inhibit in vivo the binding to human TNFα of anti-TNFα murine mAb 114 or mAb 199 or an antibody having substantially the same specific binding characteristics of mAb 114 or mAb 199, as well as fragments and regions thereof. Murine monoclonal antibodies 114, 195 and 199 and the method for producing them are described by Möller, A. et al. (*Cytokine* 2(3):162-169 (1990)), the teachings of which are entirely incorporated herein by reference. Preferred methods for determining mAb specificity and affinity by competitive inhibition can be found in Harlow, et al., *Antibodies: A Laboratory Manual*, Cold Spring Harbor Laboratory Press, Cold Spring Harbor, N.Y. (1988); Colligan et al., eds., *Current Protocols in Immunology*, Greene Publishing Assoc. and Wiley Interscience, New York (1992, 1993); Kozbor et al., *Immunol. Today* 4:72-79 (1983); Ausubel et al., eds. *Current Protocols in Molecular Biology*, Wiley Interscience, New York (1987, 1992, 1993); and Muller, *Meth. Enzymol.* 92:589-601 (1983), which references are entirely incorporated herein by reference.

Additional examples of monoclonal anti-TNF antibodies that can be used in the present invention are described in the art (see, e.g., Rathjen et al., International Publication No. WO 91/02078 (published Feb. 21, 1991); Rubin et al., EPO Patent Publication 0218868 (published Apr. 22, 1987); Yone et al., EPO Patent Publication 0288088 (Oct. 26, 1988); Liang, et al., *Biochem. Biophys. Res. Comm.* 137:847-854 (1986); Meager, et al., *Hybridoma* 6:305-311 (1987); Fendly et al., *Hybridoma* 6:359-369 (1987); Bringman, et al., *Hybridoma* 6:489-507 (1987); Hirai, et al., *J. Immunol. Meth.* 96:57-62 (1987); Moller, et al., *Cytokine* 2:162-169 (1990), which references are entirely incoporated herein by reference).

Chimeric antibodies are immunoglobulin molecules characterized by two or more segments or portions derived from different animal species. Generally, the variable region of the chimeric antibody is derived from a non-human mammalian antibody, such as a murine mAb, and the immunoglobulin constant region is derived from a human immunoglobulin molecule. Preferably, a variable region with low immunogenicity is selected and combined with a human constant region which also has low immunogenicity, the combination also preferably having low immunogenicity. "Low" immunogenicity is defined herein as raising significant HACA or HAMA responses in less than about 75%, or preferably less than about 50% of the patients treated and/or raising low titres in the patient treated (less than about 300, preferably less than about 100 measured with a double antigen enzyme immunoassay) (Elliott et al., *Lancet* 344:1125-1127 (1994), incorporated herein by reference).

As used herein, the term "chimeric antibody" includes monovalent, divalent or polyvalent immunoglobulins. A monovalent chimeric antibody is a dimer (HL)) formed by a chimeric H chain associated through disulfide bridges with a chimeric L chain. A divalent chimeric antibody is a tetramer (H2L2) formed by two HL dimers associated through at least one disulfide bridge. A polyvalent chimeric antibody can also be produced, for example, by employing a CH region that aggregates (e.g., from an IgM H chain, or μ chain).

Antibodies comprise individual heavy (H) and/or light (L) immunoglobulin chains. A chimeric H chain comprises an antigen binding region derived from the H chain of a non-human antibody specific for TNF, which is linked to at least a portion of a human H chain C region (CH), such as CH1 or CH2. A chimeric L chain comprises an antigen binding region derived from the L chain of a non-human antibody specific for TNF, linked to at least a portion of a human L chain C region (CL).

Chimeric antibodies and methods for their production have been described in the art (Morrison et al., *Proc. Natl. Acad. Sci. USA* 81:6851-6855 (1984); Boulianne et al., *Nature* 312:643-646 (1984); Neuberger et al., *Nature* 314:268-270 (1985); Taniguchi et al., European Patent Application 171496 (published Feb. 19, 1985); Morrison et al., European Patent Application 173494 (published Mar. 5, 1986); Neuberger et al., PCT Application WO 86/01533, (published Mar. 13, 1986); Kudo et al., European Patent Application 184187 (published Jun. 11, 1986); Morrison et al., European Patent Application 173494 (published Mar. 5, 1986); Sahagan et al., *J. Immunol.* 137:1066-1074 (1986); Robinson et al., International Publication No. PCT/US86/02269 (published 7May 1987); Liu et al., *Proc. Natl. Acad. Sci. USA* 84:3439-3443 (1987); Sun et al., *Proc. Natl. Acad. Sci. USA* 84:214-218 (1987); Better et al., *Science* 240:1041-1043 (1988); and Harlow and Lane, Antibodies: A Laboratory Manual, Cold Spring Harbor Laboratory, New York, 1988). These references are entirely incorporated herein by reference.

The anti-TNF chimeric antibody can comprise, for example, two light chains and two heavy chains, each of the chains comprising at least part of a human constant region and at least part of a variable (V) region of non-human origin having specificity to human TNF, said antibody binding with high affinity to an inhibiting and/or neutralizing epitope of human TNF, such as the antibody cA2. The antibody also includes a fragment or a derivative of such an antibody, such as one or more portions of the antibody chain, such as the heavy chain constant or variable regions, or the light chain constant or variable regions.

Humanizing and resurfacing the antibody can further reduce the immunogenicity of the antibody. See, for example, Winter (U.S. Pat. No. 5,225,539 and EP 239,400 B1), Padlan et al. (EP 519,596 A1) and Pedersen et al. (EP 592,106 A1). These references are incorporated herein by reference.

Preferred antibodies useful in the methods of the present invention are high affinity human-murine chimeric anti-TNF antibodies, and fragments or regions thereof, that have potent inhibiting and/or neutralizing activity in vivo against human TNFα. Such antibodies and chimeric antibodies can include those generated by immunization using purified recombinant TNFα or peptide fragments thereof comprising one or more epitopes.

An example of such a chimeric antibody is cA2 and antibodies which will competitively inhibit in vivo the binding to human TNFα of anti-TNFα murine mAb A2, chimeric mAb cA2, or an antibody having substantially the same specific binding characteristics, as well as fragments and regions thereof. Chimeric mAb cA2 has been described, for example, in U.S. application Ser. No. 08/192,093 (filed Feb. 4, 1994), U.S. application Ser. No. 08/192,102 (filed Feb. 4, 1994now U.S. Pat No. 5,656,272), U.S. application Ser. No. 08/192,861 (filed Feb. 4, 1994, now U.S. Pat. No. 5,919,452), and U.S. application Ser. No. 08/324,799 (filed Oct. 18, 1994, now U.S. Pat. No. 5,698,195, and by Le, J. et al. (International Publication No. WO 92/16553 (published Oct. 1, 1992);

Knight, D. M. et al. (*Mol. Immunol.* 30:1443-1453 (1993)); and Siegel, S. A. et al. (*Cytokine* 7(l):15-25 (1995)). These references are entirely incorporated herein by reference.

Chimeric A2 anti-TNF consists of the antigen binding variable region of the high-affinity neutralizing mouse antihuman TNF IgGl antibody, designated A2, and the constant regions of a human IgGl, kappa immunoglobulin. The human IgGl Fc region improves allogeneic antibody effector function, increases the circulating serum half-life and decreases the immunogenicity of the antibody. The avidity and epitope specificity of the chimeric A2 is derived from the variable region of the murine A2. Chimeric A2 neutralizes the cytotoxic effect of both natural and recombinant human TNF in a dose dependent manner. From binding assays of cA2 and recombinant human TNF, the affinity constant of cA2 was calculated to be $1.8 \times 10^9 M^{-1}$. Preferred methods for determining mAb specificity and affinity by competitive inhibition can be found in Harlow, et al., *Antibodies: A Laboratory Manual*, Cold Spring Harbor Laboratory Press, Cold Spring Harbor, N.Y., 1988; Colligan et al., eds., *Current Protocols in Immunology*, Greene Publishing Assoc. and Wiley Interscience, New York, (1992, 1993); Kozbor et al., *Immunol. Today* 4:72-79 (1983); Ausubel et al., eds. *Current Protocols in Molecular Biology*, Wiley Interscience, New York (1987, 1992, 1993); and Muller, *Meth. Enzymol.* 92:589-601 (1983), which references are entirely incorporated herein by reference.

As used herein, the term "antigen binding region" refers to that portion of an antibody molecule which contains the amino acid residues that interact with an antigen and confer on the antibody its specificity and affinity for the antigen. The antibody region includes the "framework" amino acid residues necessary to maintain the proper conformation of the antigen-binding residues. Generally, the antigen binding region will be of murine origin. In other embodiments, the antigen binding region can be derived from other animal species, such as sheep, rabbit, rat or hamster. Preferred sources for the DNA encoding such a non-human antibody include cell lines which produce antibody, preferably hybrid cell lines commonly known as hybridomas. In one embodiment, a preferred hybridoma is the A2 hybridoma cell line.

An "antigen" is a molecule or a portion of a molecule capable of being bound by an antibody which is additionally capable of inducing an animal to produce antibody capable of selectively binding to an epitope of that antigen. An antigen can have one or more than one epitope.

The term "epitope" is meant to refer to that portion of the antigen capable of being recognized by and bound by an antibody at one or more of the antibody's antigen binding region. Epitopes usually consist of chemically active surface groupings of molecules such as amino acids or sugar side chains and have specific three dimensional structural characteristics as well as specific charge characteristics. By "inhibiting and/or neutralizing epitope" is intended an epitope, which, when bound by an antibody, results in loss of biological activity of the molecule containing the epitope, in vivo or in vitro, more preferably in vivo, including binding of TNF to a TNF receptor. Epitopes of TNF have been identified within amino acids 1 to about 20, about 56 to about 77, about 108 to about 127 and about 138 to about 149. Preferably, the antibody binds to an epitope comprising at least about 5 amino acids of TNF within TNF residues from about 87 to about 107, about 59 to about 80 or a combination thereof. Generally, epitopes include at least about 5 amino acids and less than about 22 amino acids embracing or overlapping one or more of these regions.

For example, epitopes of TNF which are recognized by, and/or binds with anti-TNF activity, an antibody, and fragments, and variable regions thereof, include:

59-80: Tyr-Ser-Gln-Val-Leu-Phe-Lys-Gly-Gln-Gly-Cys-Pro-Ser-Thr-His-Val-Leu-Leu-Thr-His-Thr-Ile (SEQ ID NO:1); and/or 87-108: Tyr-Gln-Thr-Lys-Val-Asn-Leu-Leu-Ser-Ala-Ile-Lys-Ser-Pro-Cys-Gln-Arg-Glu-Thr-Pro-Glu-Gly (SEQ ID NO:2).

The anti-TNF antibodies, and fragments, and variable regions thereof, that are recognized by, and/or binds with anti-TNF activity, these epitopes block the action of TNFα without binding to the putative receptor binding locus as presented by Eck and Sprang (*J. Biol. Chem.* 264(29): 17595-17605 (1989) (amino acids 11-13, 37-42, 49-57 and 155-157 of hTNFα). Rathjen et al., International Publication WO 91/02078 (published Feb. 21, 1991), incorporated herein by reference, discloses TNF ligands which can bind additional epitopes of TNF.

Antibody Production Using Hybridomas

The techniques to raise antibodies to small peptide sequences that recognize and bind to those sequences in the free or conjugated form or when presented as a native sequence in the context of a large protein are well known in the art. Such antibodies can be produced by hybridoma or recombinant techniques known in the art.

Murine antibodies which can be used in the preparation of the antibodies useful in the methods of the present invention have also been described in Rubin et al., EP0218868 (published Apr. 22, 1987); Yone et al., EP0288088 (published Oct. 26, 1988); Liang, et al., *Biochem. Biophys. Res. Comm.* 137: 847-854 (1986); Meager, et al., *Hybridoma* 6:305-311 (1987); Fendly et al., *Hybridoma* 6:359-369 (1987); Bringman, et al., *Hybridoma* 6:489-507 (1987); Hirai, et al., *J. Immunol. Meth.* 96:57-62 (1987); Möller, et al., *Cytokine* 2:162-169 (1990).

The cell fusions are accomplished by standard procedures well known to those skilled in the field of immunology. Fusion partner cell lines and methods for fusing and selecting hybridomas and screening for mAbs are well known in the art. See, e.g, Ausubel infra, Harlow infra, and Colligan infra, the contents of which references are incorporated entirely herein by reference.

The TNFα-specific murine mAb useful in the methods of the present invention can be produced in large quantities by injecting hybridoma or transfectoma cells secreting the antibody into the peritoneal cavity of mice and, after appropriate time, harvesting the ascites fluid which contains a high titer of the mAb, and isolating the mAb therefrom. For such in vivo production of the mAb with a hybridoma (e.g., rat or human), hybridoma cells are preferably grown in irradiated or athymic nude mice. Alternatively, the antibodies can be produced by culturing hybridoma or transfectoma cells in vitro and isolating secreted mAb from the cell culture medium or recombinantly, in eukaryotic or prokaryotic cells.

In one embodiment, the antibody used in the methods of the present invention is a mAb which binds amino acids of an epitope of TNF recognized by A2, rA2 or cA2, produced by a hybridoma or by a recombinant host. In another embodiment, the antibody is a chimeric antibody which recognizes an epitope recognized by A2. In still another embodiment, the antibody is a chimeric antibody designated as chimeric A2 (cA2).

As examples of antibodies useful in the methods of the present invention, murine mAb A2 is produced by a cell line designated c134A. Chimeric antibody cA2 is produced by a cell line designated c168A.

"Derivatives" of the antibodies including fragments, regions or proteins encoded by truncated or modified genes to yield molecular species functionally resembling the immunoglobulin fragments are also useful in the methods of the present invention. The modifications include, but are not limited to, addition of genetic sequences coding for cytotoxic proteins such as plant and bacterial toxins. The fragments and derivatives can be produced from appropriate cells, as is known in the art. Alternatively, anti-TNF antibodies, fragments and regions can be bound to cytotoxic proteins or compounds in vitro, to provide cytotoxic anti-TNF antibodies which would selectively kill cells having TNF on their surface.

"Fragments" of the antibodies include, for example, Fab, Fab', F(ab')2 and Fv. These fragments lack the Fc fragment of intact antibody, clear more rapidly from the circulation, and can have less non-specific tissue binding than an intact antibody (Wahl et al., *J. Nucl. Med.* 24:316-325 (1983)). These fragments are produced from intact antibodies using methods well known in the art, for example by proteolytic cleavage with enzymes such as papain (to produce Fab fragments) or pepsin (to produce F(ab')2 fragments).

Recombinant Expression of Anti-TNF Antibodies

Recombinant and/or chimeric murine-human or human-human antibodies that inhibit TNF can be produced using known techniques based on the teachings provided in U.S. application Ser. No. 08/192,093 (filed Feb. 4, 1994), U.S. application Ser. No. 08/192,102 (filed Feb. 4, 1994, now U.S. Pat. No. 5,656,272), U.S. application Ser. No. 08/192,861 (filed Feb. 4, 1994, now U.S. Pat. No. 5,919,452), U.S. application Ser. No. 08/324,799 (filed on Oct. 18, 1994, now U.S. Pat. No. 5,698,195, and Le, J. et al., International Publication No. WO 92/16553 (published Oct. 1, 1992), which references are entirely incorporated herein by reference. See, e.g., Ausubel et al., eds. *Current Protocols in Molecular Biology*, Wiley Interscience, N.Y. (1987, 1992, 1993); and Sambrook et al. *Molecular Cloning: A Laboratory Manual*, Cold Spring Harbor Laboratory Press (1989), the contents of which are entirely incorporated herein by reference. See also, e.g., Knight, D. M., et al., *Mol. Immunol* 30:1443-1453 (1993); and Siegel, S. A., et al., *Cytokine* 7(1):15-25 (1995), the contents of which are entirely incorporated herein by reference.

The DNA encoding an anti-TNF antibody can be genomic DNA or cDNA which encodes at least one of the heavy chain constant region (Hc), the heavy chain variable region (Hc), the light chain variable region (Lv) and the light chain constant regions (Lc). A convenient alternative to the use of chromosomal gene fragments as the source of DNA encoding the murine V region antigen-binding segment is the use of cDNA for the construction of chimeric immunoglobulin genes, e.g., as reported by Liu et al. (*Proc. Natl. Acad. Sci., USA* 84:3439 (1987) and *J. Immunology* 139:3521 (1987), which references are entirely incorporated herein by reference. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems. An example of such a preparation is set forth below.

Because the genetic code is degenerate, more than one codon can be used to encode a particular amino acid. Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic or prokaryotic cells expressing an anti-TNF antibody or fragment. Such "codon usage rules" are disclosed by Lathe, et al., *J. Mol. Biol.* 183:1-12 (1985). Using the "codon usage rules" of Lathe, a single oligonucleotide, or a set of oligonucleotides, that contains a theoretical "most probable" nucleotide sequence capable of encoding anti-TNF variable or constant region sequences is identified.

Although occasionally an amino acid sequence can be encoded by only a single oligonucleotide, frequently the amino acid sequence can be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the protein.

The oligonucleotide, or set of oligonucleotides, containing the theoretical "most probable" sequence capable of encoding an anti-TNF antibody or fragment including a variable or constant region is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the variable or constant region anti-TNF gene (Sambrook et al., infra).

A suitable oligonucleotide, or set of oligonucleotides, which is capable of encoding a fragment of the variable or constant anti-TNF region (or which is complementary to such an oligonucleotide, or set of oligonucleotides) is identified (using the above-described procedure), synthesized, and hybridized by means well known in the art, against a DNA or, more preferably, a cDNA preparation derived from cells which are capable of expressing anti-TNF antibodies or variable or constant regions thereof. Single stranded oligonucleotide molecules complementary to the "most probable" variable or constant anti-TNF region peptide coding sequences can be synthesized using procedures which are well known to those of ordinary skill in the art (Belagaje, et al., *J. Biol. Chem.* 254:5765-5780 (1979); Maniatis, et al., In: *Molecular Mechanisms in the Control of Gene Expression*, Nierlich, et al., Eds., Acad. Press, NY (1976); Wu, et al., *Prog. Nucl. Acid Res. Molec. Biol.* 21:101-141 (1978); Khorana, *Science* 203: 614-625 (1979)). Additionally, DNA synthesis can be achieved through the use of automated synthesizers. Techniques of nucleic acid hybridization are disclosed by Sambrook et al., *Molecular Cloning: A Laboratory Manual*, Cold Spring Harbor Laboratory Press (1989); and by Haynes, et al., in: *Nucleic Acid Hybridization, A Practical Approach*, IRL Press, Washington, D.C. (1985), which references are entirely incorporated herein by reference. Techniques such as, or similar to, those described above have successfully enabled the cloning of genes for human aldehyde dehydrogenases (Hsu, et al., *Proc. Natl. Acad. Sci. USA* 82:3771-3775 (1985)), fibronectin (Suzuki, et al., *Bur. Mol. Biol. Organ. J.* 4:2519-2524 (1985)), the human estrogen receptor gene (Walter, et al., *Proc. Natl. Acad. Sci. USA* 82:7889-7893 (1985)), tissue-type plasminogen activator (Pennica, et al., *Nature* 301:214-221 (1983)) and human placental alkaline phosphatase complementary DNA (Keun, et al., *Proc. Natl. Acad. Sci. USA* 82:8715-8719 (1985)).

In an alternative way of cloning a polynucleotide encoding an anti-TNF variable or constant region, a library of expression vectors is prepared by cloning DNA or, more preferably, cDNA (from a cell capable of expressing an anti-TNF antibody or variable or constant region) into an expression vector. The library is then screened for members capable of expressing a protein which competitively inhibits the binding of an anti-TNF antibody, such as A2 or cA2, and which has a nucleotide sequence that is capable of encoding polypeptides that have the same amino acid sequence as anti-TNF antibodies or fragments thereof. In this embodiment, DNA, or more preferably cDNA, is extracted and purified from a cell which is capable of expressing an anti-TNF antibody or fragment. The purified cDNA is fragmentized (by shearing, endonuclease digestion, etc.) to produce a pool of DNA or cDNA fragments. DNA or CDNA fragments from this pool are then cloned into an expression vector in order to produce a genomic library of expression vectors whose members each contain a unique cloned DNA or CDNA fragment such as in a lambda phage library, expression in prokaryotic cell (e.g., bacteria) or eukaryotic cells, (e.g., mammalian, yeast, insect or, fungus). See, e.g., Ausubel, infra, Harlow, infra, Colligan, infra; Nyyssonen et al. *Bio/Technology* 11:591-595 (1993); Marks et al., *Bio/Technology* 11:1145-1149 (October 1993). Once nucleic acid encoding such variable or constant anti-TNF regions is isolated, the nucleic acid can be appropriately expressed in a host cell, along with other constant or variable heavy or light chain encoding nucleic acid, in order to provide recombinant monoclonal antibodies that bind TNF with inhibitory activity. Such antibodies preferably include a murine or human anti-TNF variable region which contains a framework residue having complementarity determining residues which are responsible for antigen binding.

Human genes which encode the constant (C) regions of the chimeric antibodies, fragments and regions of the present invention can be derived from a human fetal liver library, by known methods. Human C region genes can be derived from any human cell including those which express and produce human immunoglobulins. The human CH region can be derived from any of the known classes or isotypes of human H chains, including gamma, $\mu$, $\alpha$, $\delta$ or $\epsilon$, and subtypes thereof, such as G1, G2, G3 and G4. Since the H chain isotype is responsible for the various effector functions of an antibody, the choice of CH region will be guided by the desired effector functions, such as complement fixation, or activity in antibody-dependent cellular cytotoxicity (ADCC). Preferably, the CH region is derived from gamma 1 (IgG1), gamma 3 (IgG3), gamma 4 (IgG4), or $\mu$ (IgM). The human CL region can be derived from either human L chain isotype, kappa or lambda.

Genes encoding human immunoglobulin C regions are obtained from human cells by standard cloning techniques (Sambrook, et al. (*Molecular Cloning: A Laboratory Manual*, 2nd Edition, Cold Spring Harbor Press, Cold Spring Harbor, N.Y. (1989) and Ausubel et al., eds., *Current Protocols in Molecular Biology* (1987-1993)). Human C region genes are readily available from known clones containing genes representing the two classes of L chains, the five classes of H chains and subclasses thereof. Chimeric antibody fragments, such as F(ab')$_2$ and Fab, can be prepared by designing a chimeric H chain gene which is appropriately truncated. For example, a chimeric gene encoding an H chain portion of an F(ab')$_2$ fragment would include DNA sequences encoding the CH1 domain and hinge region of the H chain, followed by a translational stop codon to yield the truncated molecule.

Generally, the murine, human and chimeric antibodies, fragments and regions are produced by cloning DNA segments encoding the H and L chain antigen-binding regions of a TNF-specific antibody, and joining these DNA segments to DNA segments encoding CH and CL regions, respectively, to produce murine, human or chimeric immunoglobulin-encoding genes. Thus, in a preferred embodiment, a fused chimeric gene is created which comprises a first DNA segment that encodes at least the antigen-binding region of non-human origin, such as a functionally rearranged V region with joining (J) segment, linked to a second DNA segment encoding at least a part of a human C region.

Therefore, cDNA encoding the antibody V and C regions and the method of producing a chimeric antibody can involve several steps, outlined below:

1. isolation of messenger RNA (mRNA) from the cell line producing an anti-TNF antibody and from optional additional antibodies supplying heavy and light constant regions; cloning and cDNA production therefrom;
2. preparation of a full length cDNA library from purified mRNA from which the appropriate V and/or C region gene segments of the L and H chain genes can be: (i) identified with appropriate probes, (ii) sequenced, and (iii) made compatible with a C or V gene segment from another antibody for a chimeric antibody;
3. Construction of complete H or L chain coding sequences by linkage of the cloned specific V region gene segments to cloned C region gene, as described above;
4. Expression and production of L and H chains in selected hosts, including prokaryotic and eukaryotic cells to provide murine-murine, human-murine, human-human or human-murine antibodies.

One common feature of all immunoglobulin H and L chain genes and their encoded mRNAs is the J region. H and L chain J regions have different sequences, but a high degree of sequence homology exists (greater than 80%) among each group, especially near the C region. This homology is exploited in this method and consensus sequences of H and L chain J regions can be used to design oligonucleotides for use as primers for introducing useful restriction sites into the J region for subsequent linkage of V region segments to human C region segments.

C region cDNA vectors prepared from human cells can be modified by site-directed mutagenesis to place a restriction site at the analogous position in the human sequence. For example, one can clone the complete human kappa chain C (Ck) region and the complete human gamma-1 C region (C gamma-1). In this case, the alternative method based upon genomic C region clones as the source for C region vectors would not allow these genes to be expressed in bacterial systems where enzymes needed to remove intervening sequences are absent. Cloned V region segments are excised and ligated to L or H chain C region vectors. Alternatively, the human C gamma-1 region can be modified by introducing a termination codon thereby generating a gene sequence which encodes the H chain portion of an Fab molecule. The coding sequences with linked V and C regions are then transferred into appropriate expression vehicles for expression in appropriate hosts, prokaryotic or eukaryotic.

Two coding DNA sequences are said to be "operably linked" if the linkage results in a continuously translatable sequence without alteration or interruption of the triplet reading frame. A DNA coding sequence is operably linked to a gene expression element if the linkage results in the proper function of that gene expression element to result in expression of the coding sequence.

Expression vehicles include plasmids or other vectors. Preferred among these are vehicles carrying a functionally complete human CH or CL chain sequence having appropriate restriction sites engineered so that any VH or VL chain sequence with appropriate cohesive ends can be easily inserted therein. Human CH or CL chain sequence-containing vehicles thus serve as intermediates for the expression of any desired complete H or L chain in any appropriate host.

A chimeric antibody, such as a mouse-human or human-human, will typically be synthesized from genes driven by the chromosomal gene promoters native to the mouse H and L chain V regions used in the constructs; splicing usually occurs between the splice donor site in the mouse J region and the splice acceptor site preceding the human C region and also at the splice regions that occur within the human C, region; polyadenylation and transcription termination occur at native chromosomal sites downstream of the human coding regions.

A nucleic acid sequence encoding at least one anti-TNF antibody fragment may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Ausubel, supra, Sambrook, supra, entirely incorporated herein by reference, and are well known in the art.

A nucleic acid molecule, such as DNA, is "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as anti-TNF peptides or antibody fragments in recoverable amounts. The precise nature of the regulatory regions needed for gene expression may vary from organism to organism and is well known in the analogous art. See, e.g., Sambrook et al., *Molecular Cloning: A Laboratory Manual*, Cold Spring Harbor Laboratory Press (1989); and Ausubel, eds. *Current Protocols in Molecular Biology*, Wiley Interscience (1987, 1993).

Many vector systems are available for the expression of cloned anti-TNF peptide H and L chain genes in mammalian cells (see Glover, ed., *DNA Cloning, Vol. II*, pp143-238, IRL Press, 1985). Different approaches can be followed to obtain complete H2L2 antibodies. It is possible to co-express H and L chains in the same cells to achieve intracellular association and linkage of H and L chains into complete tetrameric H2L2 antibodies. The co-expression can occur by using either the same or different plasmids in the same host. Genes for both H and L chains can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing H2L2 molecules via either route could be transfected with plasmids encoding additional copies of peptides, H, L, or H plus L chains in conjunction with additional selectable markers to generate cell lines with enhanced properties, such as higher production of assembled H2L2 antibody molecules or enhanced stability of the transfected cell lines.

Receptor Molecules

Receptor molecules useful in the methods of the present invention are those that bind TNF with high affinity (see, e.g., Feldmann et al., International Publication No. WO 92/07076 (published Apr. 30, 1992), incorporated herein by reference) and possess low immunogenicity. In particular, the 55 kDa (p55 TNF-R) and the 75 kDa (p75 TNF-R) TNF cell surface receptors are useful in the present invention. Truncated forms of these receptors, comprising the extracellular domains (ECD) of the receptors or functional portions thereof, are also useful in the present invention. Truncated forms of the TNF receptors, comprising the ECD, have been detected in urine and serum as 30 kDa and 40 kDa TNF inhibitory binding proteins (Engelmann, H., et al., *J. Biol. Chem.* 265:1531-1536 (1990)). TNF receptor multimeric molecules and TNF immunoreceptor fusion molecules, and derivatives and fragments or portions thereof, are additional examples of receptor molecules which are useful in the methods of the present invention. The receptor molecules which can be used in the invention are characterized by their ability to treat patients for extended periods with good to excellent alleviation of symptoms and low toxicity. Low immunogenicity and/or high affinity, as well as other undefined properties, may contribute to the therapeutic results achieved.

TNF receptor multimeric molecules useful in the present invention comprise all or a functional portion of the ECD of two or more TNF receptors linked via one or more polypeptide linkers. The multimeric molecules can further comprise a signal peptide of a secreted protein to direct expression of the multimeric molecule. These multimeric molecules and methods for their production have been described in U.S. application Ser. No. 08/437,533 (filed May 9, 1995), the content of which is entirely incorporated herein by reference.

TNF immunoreceptor fusion molecules useful in the methods of the present invention comprise at least one portion of one or more immunoglobulin molecules and all or a functional portion of one or more TNF receptors. These immunoreceptor fusion molecules can be assembled as monomers, or hetero- or homo-multimers. The immunoreceptor fusion molecules can also be monovalent or multivalent.

TNF immunoreceptor fusion molecules and methods for their production have been described in the art (Lesslauer et al., *Eur. J. Immunol.* 21:2883-2886 (1991); Ashkenazi et al., *Proc. Natl. Acad. Sci. USA* 88:10535-10539 (1991); Peppel et al., *J. Exp. Med.* 174:1483-1489 (1991); Kolls et al., *Proc. Natl. Acad. Sci. USA* 91:215-219 (1994); Butler et al. *Cytokine* 6(6):616-623 (1994); Baker et al., *Eur. J. Immunol.* 24:2040-2048 (1994); Beutler et al., U.S. Pat. No. 5,447,851; and U.S. patent application Ser. No. 08/442,133 (filed May 16, 1995)). These references are entirely incorporated herein by reference. Methods for producing immunoreceptor fusion molecules can also be found in Capon et al., U.S. Pat. No. 5,116,964; Capon et al., U.S. Pat. No. 5,225,538; and Capon et al., *Nature* 337:525-531 (1989), which references are entirely incorporated herein by reference.

Derivatives, fragments, regions and functional portions of the receptor molecules functionally resemble the receptor molecules that can be used in the present invention (i.e., they bind TNF with high affinity and possess low immunogenicity). A functional equivalent or derivative of the receptor molecule refers to the portion of the receptor molecule, or the portion of the receptor molecule sequence which encodes the receptor molecule, that is of sufficient size and sequences to functionally resemble the receptor molecules that can be used in the present invention (i.e., bind TNF with high affinity and possess low immunogenicity). A functional equivalent of the receptor molecule also includes modified receptor molecules that functionally resemble the receptor molecules that can be used in the present invention (i.e., bind TNF with high affinity and possess low immunogenicity). For example, a functional equivalent of the receptor molecule can contain a "SILENT" codon or one or more amino acid substitutions, deletions or additions (e.g., substitution of one acidic amino acid for another acidic amino acid; or substitution of one codon encoding the same or different hydrophobic amino acid for another codon encoding a hydrophobic amino acid). See Ausubel et al., *Current Protocols in Molecular Biology*, Greene Publishing Assoc. and Wiley-Interscience (1989).

Administration

TNF antagonists can be administered to an individual in a variety of ways. The routes of administration include intradermal, transdermal (e.g., in slow release polymers), intramuscular, intraperitoneal, intravenous, subcutaneous, oral, epidural and intranasal routes. Any other therapeutically efficacious route of administration can be used, for example, infusion or bolus injection, absorption through epithelial or mucocutaneous linings, or by gene therapy wherein a DNA molecule encoding the TNF antagonist is administered to the patient, e.g., via a vector, which causes the TNF antagonist to be expressed and secreted at therapeutic levels in vivo. In addition, the TNF antagonists can be administered together with other components of biologically active agents, such as pharmaceutically acceptable surfactants (e.g., glycerides), excipients (e.g., lactose), carriers, diluents and vehicles. If desired, certain sweetening, flavoring and/or coloring agents can also be added. The TNF antagonists can be administered prophylactically or therapeutically to an individual prior to, simultaneously with or sequentially with other therapeutic regimens or agents (e.g., multiple drug regimens), in a therapeutically effective amount. TNF antagonists that are administered simultaneously with other therapeutic agents can be administered in the same or different compositions.

For parenteral (e.g., intravenous, subcutaneous, intramuscular) administration, TNF antagonists can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by commonly used techniques.

Suitable pharmaceutical carriers are described in Remington's Pharmaceutical Sciences, A. Osol, a standard reference text in this field of art.

For example, a parenteral composition suitable for administration by injection is prepared by dissolving 1.5% by weight of active ingredient in 0.9% sodium chloride solution.

A "therapeutically effective amount" is such that when administered, the TNF antagonist results in inhibition of the biological activity of TNF, relative to the biological activity of TNF when a therapeutically effective amount of the antagonist is not administered.

The dosage administered to an individual will vary depending upon a variety of factors, including the pharmacodynamic characteristics of the particular antagonists, and its mode and route of administration; size, age, sex, health, body weight and diet of the recipient; nature and extent of symptoms of the disease or disorder being treated, kind of concurrent treatment, frequency of treatment, and the effect desired. In vitro and in vivo methods of determining the inhibition of TNF in an individual are well known to those of skill in the art. Such in vitro assays can include a TNF cytotoxicity assay (e.g., the WEHI assay or a radioimmunoassay, ELISA). In vivo methods can include rodent lethality assays and/or primate pathology model systems (Mathison et al., *J. Clin. Invest.*, 81: 1925-1937 (1988); Beutler et al., *Science* 229: 869-871 (1985); Tracey et al., *Nature* 330: 662-664 (1987); Shimamoto et al., *Immunol. Lett.* 17: 311-318 (1988); Silva et al., *J. Infect. Dis.* 162: 421-427 (1990); Opal et al., *J. Infect. Dis.* 161: 1148-1152 (1990); Hinshaw et al., *Circ. Shock* 30: 279-292 (1990)).

TNF antagonist can be administered in single or multiple doses depending upon factors such as nature and extent of symptoms, kind of concurrent treatment and the effect desired. Thus, other therapeutic regimens or agents can be used in conjunction with the methods of the present invention. Adjustment and manipulation of established dosage ranges are well within the ability of those skilled in the art.

Usually a daily dosage of active ingredient can be about 0.01 to 100 milligrams per kilogram of body weight. Ordinarily 1 to 40 milligrams per kilogram per day given in divided doses 1 to 6 times a day or in sustained release form is effective to obtain desired results. Second or subsequent administrations can be administered at a dosage which is the same, less than or greater than the initial or previous dose administered to the individual.

A second or subsequent administration is preferably during or immediately prior to relapse or a flare-up of the disease or symptoms of the disease. For example, second and subsequent administrations can be given between about one day to 30 weeks from the previous administration. Two, three, four or more total administrations can be delivered to the individual, as needed. The terms "reoccurrence", "flare-up" or "relapse" are defined to encompass the reappearance of one or more symptoms of the disease state.

Dosage forms (composition) suitable for internal administration generally contain from about 0.1 milligram to about 500 milligrams of active ingredient per unit. In these pharmaceutical compositions the active ingredient will ordinarily be present in an amount of about 0.5-95% by weight based on the total weight of the composition.

The present invention will now be illustrated by the following example, which is not intended to be limiting in any way.

EXAMPLE

Methods

Trial Procedures

The selection of patients for this study and their treatment have been described in detail previously (Elliott et al., *Lancet* 344:1105-1110 (1994)). In brief, 73 patients meeting the revised ACR criteria for the diagnosis of RA (Arnett et al.,

*Arthritis Rheum.* 31:315-321 (1988)) were recruited from the clinics of 4 cooperating trial centers. All patients had active RA and evidence of erosive disease on X-rays of hands or feet. Patients taking disease modifying anti-rheumatic drugs were withdrawn from their therapy at least 4 weeks prior to study entry, but were permitted to continue taking low dose oral corticosteroids or non-steroidal anti-inflammatory drugs at stable dosage.

cA2 is a human/murine chimeric monoclonal antibody of IgG1κ isotype, with specificity for recombinant and natural human TNFα. Chimeric monoclonal antibody cA2 and the method for producing it is described in U.S. application Ser. No. 08/192,093 (filed Feb. 4, 1994), U.S. application Ser. No. 08/192,102 (filed Feb. 4, 1994, now U.S. Pat. No. 5,656,272), U.S. application Ser. No. 08/192,861 (filed Feb. 4, 1994, now U.S. Pat. No. 5,919,452), U.S. application Ser. No. 08/324,799 (filed on Oct. 18, 1994, now U.S. Pat. No. 5,698,195, and Le, J. et al., International Publication No. WO 92/16553 (published Oct. 1, 1992), which references are entirely incorporated herein by reference. At entry to the study, patients were randomised to receive a single 2 hour infusion of either placebo (0.1%i human serum albumin, 24 patients), low dose cA2 (1 mg/kg, 25 patients) or high dose cA2 (10 mg/kg, 24 patients) as an outpatient procedure. Patients were then followed using clinical and laboratory parameters for a period of 4 weeks. Patients, investigators and laboratory personnel were blinded as to the treatment administered.

Blood samples for measurements of cytokines and acute phase proteins were drawn prior to the infusion on day 0 and at the following times after completion of the infusion: 1 and 8 hours, 1 and 3 days, 1, 2, 3, 4, weeks. This resulted in the following mean collection times: 0830, 1300, 2000 (on day 0); 1200, 1100 (on days 1 and 3); 1030, 1100, 1045, 1045 (on weeks 1-4). Blood was collected into sterile tubes, allowed to clot for 30 minutes and spun at room temperature for 20 minutes at 2500 rpm. Serum was aliquoted into plastic tubes and stored at $-70°$ C. until assayed. Plasma was prepared from EDTA blood and handled similarly.

Laboratory Measurements

Measurement of circulating cytokines and acute phase proteins was made using commercially available assays, according to the manufacturers' directions. All samples from a given patient were assayed together, to reduce inter-assay variability.

Cytokines

IL-6 was measured by an enzyme amplified sensitivity immunoassay technique, based on an oligoclonal detection system (Medgenix Diagnostics, Brussels, Belgium). Briefly, serum samples were incubated in microtiter plates precoated with a cocktail of monoclonal antibodies to IL-6 and bound cytokine was detected by the addition of complementary monoclonal antibodies to IL-6, conjugated to horse radish peroxidase. Optical density values obtained at 450 nm were compared to those obtained for a series of standards covering the range 10-2000 pg/ml.

Acute Phase Proteins

CRP was measured by fluorescent polarisation immunoassay using the TDX system (Abbot Diagnostics, Maidenhead, UK). The system works by comparing the polarisation value obtained for a given sample to a pre-calibrated standard value. Each assay was validated by the inclusion of control sera containing known quantities of CRP.

SAA was measured by a solid phase ELISA (Biosource Inc., Camarillo, Calif.). Diluted serum samples were incubated in microtiter plates precoated with a monoclonal antibody to SAA, together with a second complementary enzyme conjugated anti-SAA monoclonal antibody. Optical density values were compared to those obtained for a series of standards covering the range 0-300 ng/ml. Levels greater than 300 ng/ml were measured by repeating the assay using further sample dilutions.

Haptoglobin was measured using radial immunodiffusion (Behring, Hounslow, UK). EDTA plasma was placed into a well cut into a gel containing antibodies to haptoglobin. After 48 hours the diameter of the resulting preciptin rings was measured and the concentration compared to a pre-determined concentration table. The assay was validated by the inclusion in each assay of control sera of known concentration.

Fibrinogen was measured using radial immunodiffusion (Behring, Hounslow, UK). EDTA plasma was placed into a well cut into a gel containing antibodies to fibrinogen. After 18 hours the diameter of the resulting precipitin ring was measured and the concentration compared to a pre-determined concentration table. The assay was validated by the inclusion in each assay of control sera of known concentration.

Statistics

Samples giving values below the assay detection limit were ascribed a value half the relevant detection limit prior to analysis. Data are expressed as median, interquartile range. Diurnal variation in IL-6 was assessed in the placebo group using the Wilcoxon signed rank test. Analysis of variance on the van der Waerden normal scores was used to compare baseline values of IL-6, CRP and SAA as well as comparison of changes from baseline at each post-treatment point. The model included terms for both investigational site and treatment group. Significant differences were further tested by Dunnett's comparison to the placebo group. The Mann Whitney U test was used to compare the haptoglobin and fibrinogen data for the placebo and high dose cA2 groups. Comparison between the percent reductions in IL-6, CRP and SAA in the high dose cA2 group was made using the Kruskal-Wallis test. Associations between parameters were defined using Spearman's rank correlation coefficient (p). No adjustment was made for multiplicity of time points or laboratory parameters. Analyses were performed on a VAX computer using SAS and on a PowerMacintosh computer using Minitab.

Results

Effect of cA2 on Haptoglobin and Fibrinogen

In order to further define the biological effects of cA2, plasma levels of haptoglobin and fibrinogen were measured as representative of later elements within the acute phase response (Table). The data are expressed as median, interquartile range, with the number of patients shown in brackets.

TABLE

| Plasma Haptoglobin and Fibrinogen | | |
|---|---|---|
| | Placebo | 10 mg/kg cA2 |
| Haptoglobin (g/l) | | |
| Day 0 | 3.4, 3.0-4.3 [20] | 3.3, 2.7-3.7 [15] |
| Day 28 | 3.4, 3.0-4.3 [20] | 2.5, 1.5-3.2 [15] |
| | | $p < 0.001$ |
| Fibrinogen (g/l) | | |
| Day 0 | 3.8, 3.4-5.0 [20] | 4.1, 3.2-4.7 [14] |
| Day 28 | 4.0, 3.3-5.4 [20] | 2.8, 2.2-3.1 [14] |
| | | $p < 0.002$ |

Normal ranges:
haptoglobin 0.7-3.8 g/l
fibrinogen 1.8-3.5 g/l.

Pre-treatment haptoglobin and fibrinogen levels were similar in the placebo and high dose cA2 treatment groups. Placebo-treated patients showed no significant change in either measure, while the high dose cA2 group showed a significant reduction in both measures by week 4 (p<0.001, p<0.002, haptoglobin and fibrinogen respectively). (p values assess significance of the change from pre-treatment values in the cA2 group compared with change in the placebo group, by Mann Whitney U test).

Effect of cA2 on Circulating IL-6

In defining the biological effects of cA2, in addition to plasma levels of fibrinogen and haptoglobin, circulating IL-6 was also measured. IL-6 was detectable in all but 4 of the 72 pre-treatment sera tested. The median, interquartile range pre-treatment circulating IL-6 levels for the 3 treatment groups were 125, 56-209 pg/ml, N=24; 130, 57-225 pg/ml, N=24; 114, 78-188 pg/ml, N=24 (placebo, low and high dose cA2 respectively, p>0.05, normal range <10 pg/ml).

The changes in circulating IL-6 following treatment are shown in FIGS. 1A and 1B (* indicates p<0.05,  indicates p<0.01, * indicates p<0.001 compared with placebo, by ANOVA). Each point represents the median change from day 0 values in up to 24 patients, with interquartile ranges omitted for clarity. Patients were treated on the morning of day 0 with a single, 2 hour infusion of either placebo (circle), 1 mg/kg cA2 (triangle) or 10 mg/kg cA2 (square).

IL-6 levels showed significant reductions in the placebo group at the 1300 and 2000 hours time points on day 0 (p<0.001, p=0.002 respectively), with partial recovery by day 1 (FIG. 1A). Patients treated with cA2 showed even more marked reductions in circulating IL-6 at 1300 hours on day 0 and continuing decline thereafter, reaching significance compared with placebo by day 1 (p<0.01, p<0.001, low and high dose cA2 respectively). In FIG. 1B, changes in serum Il-6 over the longer term are displayed. The highly significant falls in serum IL-6 seen at day 1 were maintained for the duration of the study in patients receiving high dose cA2 but there was a partial loss of effect in patients treated with low dose cA2 by week 4 (FIG. 1B).

The changes in median IL-6 values were reflected in the individual patient responses for IL-6. Of the 24 low dose cA2 patients tested, 22 had elevated IL-6 values pre-treatment and 14 of the 22 (64%) showed normalisation of values from day 1. Similarly, 23 of 24 high dose cA2 patients had elevated circulating IL-6 pre-treatment, of whom 16 (70%) normalised from day 1.

The detection of elevated circulating IL-6 in the patients is consistent with previous reports, which showed the presence of IL-6 in the majority of RA sera, although at lower concentrations than found in matched synovial fluid samples (Houssiau et al., *Arthritis Rheum.* 31:784-788 (1988); Swaak et al., *Scand. J. Rheumatol.* 17:469-474 (1988); Arvidson et al., *Ann. Rheum. Dis.* 53:521-524 (1994)). The reductions in circulating IL-6 in placebo treated patients during the course of days 0 and 1 are also consistent with the recognised diurnal variation in this cytokine in patients with RA (Arvidson et al., *Ann. Rheum. Dis.* 53:521-524 (1994)). The reductions in circulating IL-6 in cA2-treated patients were even more marked than in the placebo group, reaching significance from day 1. These findings support an earlier, preliminary report of reductions in circulating IL-6 in patients treated in the open label trial of cA2 (Elliott et al., *Arthritis Rheum.* 36:1681-1690 (1993)) and concur with the results of an open label trial of cA2 in active, refractory Crohn's disease (Van Dullemen et al., *Gastroenterology* 109:129-135 (1995)). Although all but two of the Crohn's patients studied had baseline circulating IL-6 levels within the normal range, a significant fall was seen after cA2 treatment. The results described herein provide in vivo evidence that TNFα is in part regulatory for IL-6 production in RA synovial tissue. In vitro findings also demonstrated that TNFα is in part regulatory for IL-6 production in RA synovial tissue.

Effect of cA2 on CRP and SAA

To further define the biological effects of cA2, circulating CRP and SAA levels were measured. The changes in circulating CRP values in this study have been reported previously (Elliott et al., *Lancet* 344:1105-1110 (1994)). In brief, patients treated with placebo showed no significant change in CRP values, while those treated with either low or high dose cA2 showed large and highly significant reductions, evident as early as day 1 post-treatment and reaching their maximal extent by day 7. The median, interquartile range pre-treatment CRP values were: 56, 33-70 mg/l; 58, 34-84 mg/l; 65, 28-94 mg/l (placebo, low and high dose cA2 groups, respectively, p>0.05, normal range <10 mg/l) and by day 7 the equivalent values were: 56, 31-72 mg/l; 21, 16-25 mg/l; 18, 13-35 mg/l (p<0.001 for both low and high dose cA2, compared with placebo).

Changes in circulating SAA following treatment with cA2 are shown in FIG. 2 (* indicates p<0.05,  indicates p<0.01, * indicates p<0.001 compared with placebo, by ANOVA). Each point represents the median change from day 0 values in up to 24 patients, with interquartile ranges omitted for clarity. Patients were treated on the morning of day 0 with a single, 2 hour infusion of either placebo (circle), 1 mg/kg cA2 (triangle) or 10 mg/kg cA2 (square).

Pre-treatment circulating SAA showed a tendency to higher values in the 1 mg/kg cA2 group than in other treatment groups (335, 62-750 mg/l, N-24; 591, 188-1130 mg/l, N=25; 378, 180-935 mg/l, N=24; placebo, low and high dose cA2 respectively; normal range<10 mg/l), although this difference was not statistically significant. No significant changes in SAA levels were seen following treatment in the placebo group (FIG. 2), while those patients treated with either low or high dose cA2 showed large and highly significant reductions. These changes were less rapid than those seen for IL-6, with maximal improvements delayed until day 3 (FIG. 2). A trend towards a loss of response in SAA for patients treated with low dose cA2 was noted towards the end of the study (FIG. 2).

Association between Circulating IL-6 and Acute Phase Proteins

Figure 3:
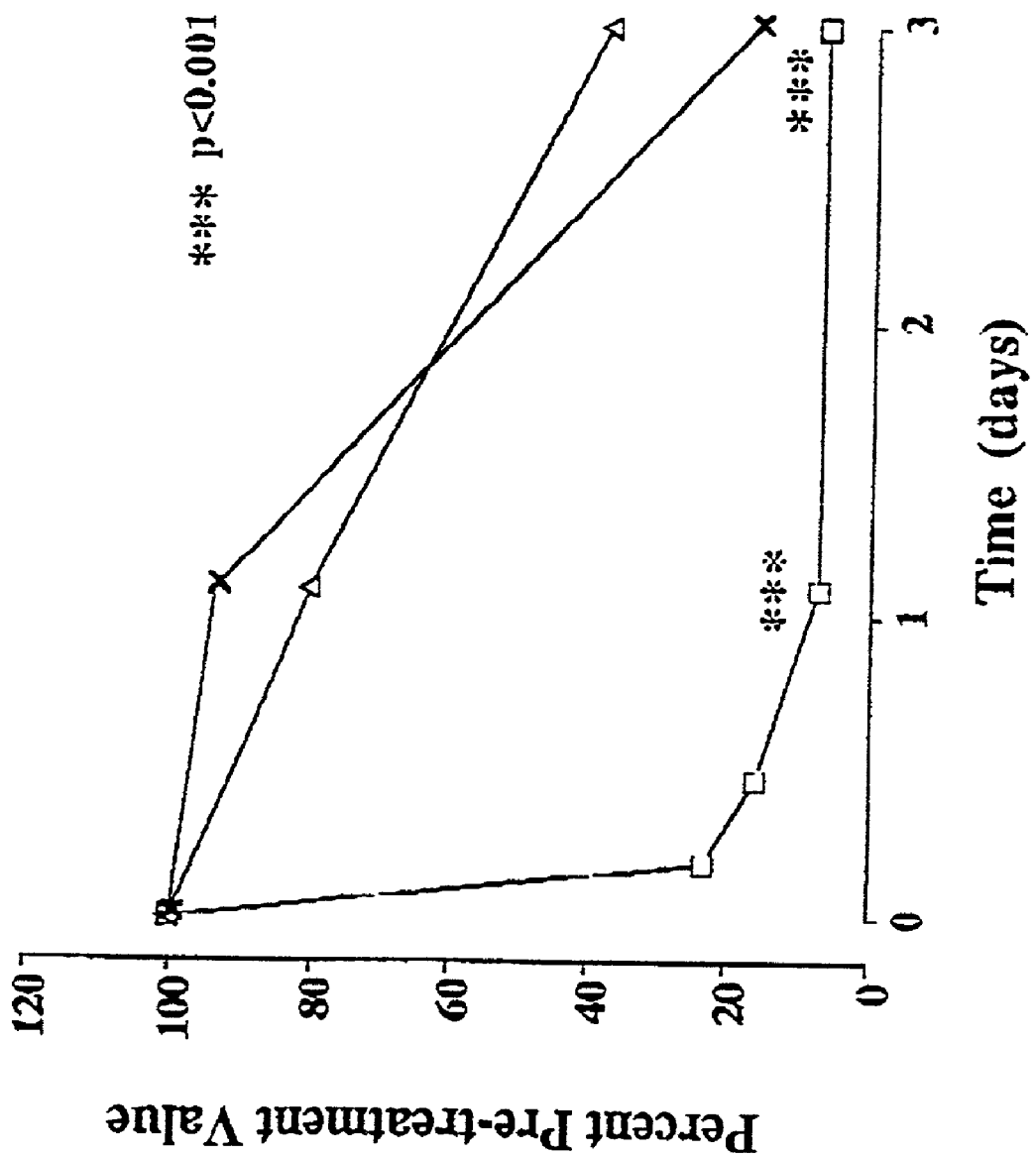
FIG. 3 is a graphic representation of results showing the rate of change in circulation IL-6 and acute phase proteins.

Because IL-6 is the principal regulator of hepatic acute phase protein synthesis in vitro (Gauldie et al., *Proc. Natl. Acad. Sci. USA* 84:7251-7255 (1987); Baumann et al., *Immunol. Today* 15:74-80 (1994)), the association between IL-6, two acute phase reactants, CRP and SAA, was tested in the patients. A comparison of the kinetics of change in each of these mediators following treatment with high dose cA2 is shown in FIG. 3. Each point represents the median of values from 24 patients, expressed as a percentage of the pre-treatment values. Square=circulating IL-6, triangle=CRP, and X=SAA before (day 0) and after treatment with a single, 2 hour infusion of high dose cA2 (10 mg/kg). *** indicates p<0.001, comparing IL-6, CRP and SAA, by Kruskal-Wallis test.

By day 1, median circulating IL-6 values had fallen compared with pre-treatment values by 95%, whereas reductions in CRP (20%) and SAA (5%) were much more modest (p<0.001). Although the median values for the two acute phase proteins had fallen further by day 3, thereby narrowing the gap with IL-6, the reduction in IL-6 at this time was still significantly greater than for the acute phase proteins (p<0.001). This temporal relationship is consistent with regulation of CRP and SAA production by IL-6, but interpretation of the results is complicated by marked differences in the circulating half times of these molecules (Castell et al., *Eur. J. Biochem.* 177:357-361 (1988); Vigushin et al., *J. Clin.Invest.* 91:1351-1357 (1993)). The demonstration of significant correlations between both pre-treatment day 3 reductions in serum IL-6 and the corresponding values for the acute phase proteins provides further evidence for a relationship between these mediators.

Figure 4A:
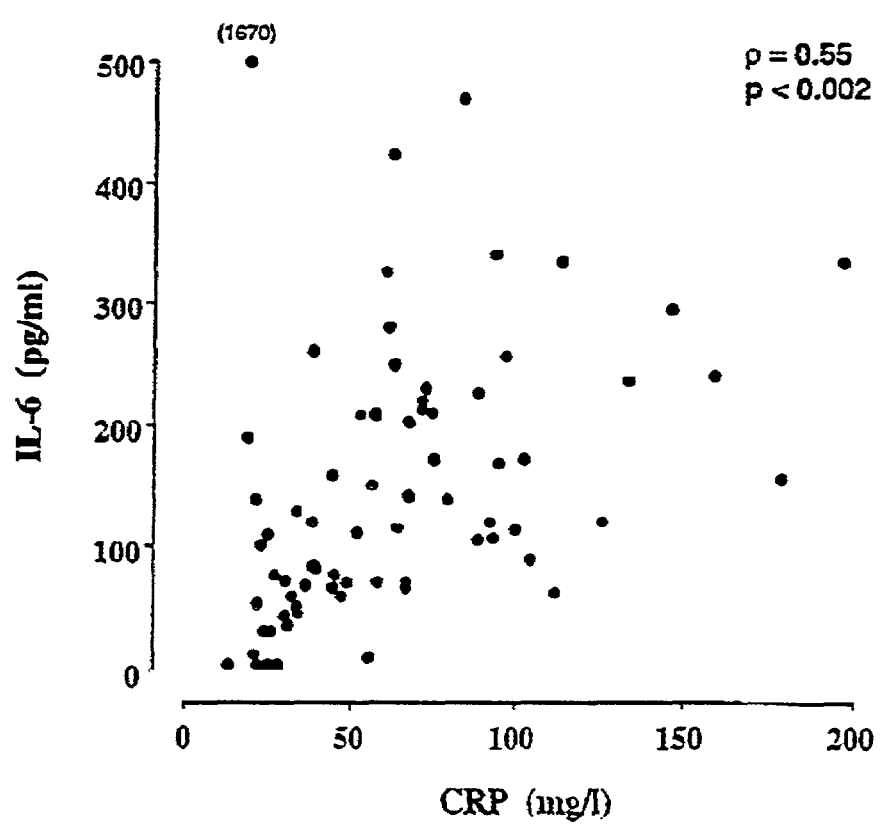
FIGS. 4A-4B are scatter graph representations showing the relationship between circulating IL-6 and C reactive protein (CRP).
Figure 4B:
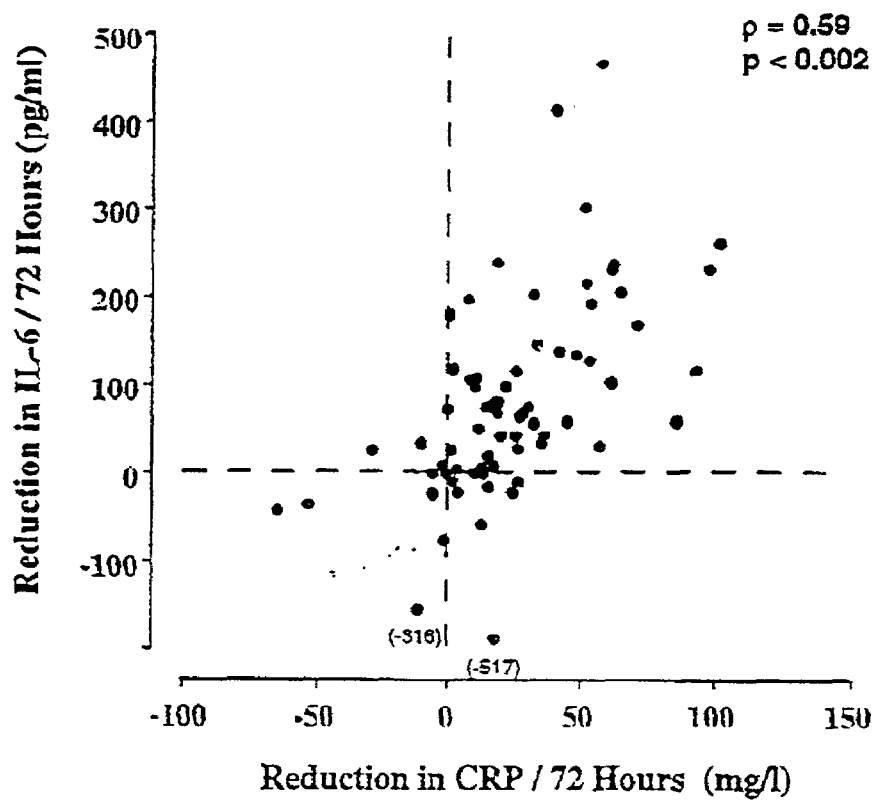

A scatter graph comparing pre-treatment IL-6 and CRP levels in all 73 patients is shown in FIG. 4A, indicating a moderate association between these variables (p=0.55, p<0.002). A similar association was found when comparing the reduction in circulating IL-6 by day 3 with the reduction in CRP over the same time period (FIG. 4B; p=0.59, p<0.002). (Each point in FIGS. 4A-4B represents an individual patient.) An association between circulating IL-6 levels and CRP in patients with inflammatory arthritis has been noted previously (Arvidson et al., *Ann. Rheum. Dis.* 53:521-524 (1994)). It is possible that other circulating cytokines with hepatocyte stimulating activity, such as leukemia inhibitory factor, may also contribute to acute phase protein synthesis in RA.

Less impressive, but still statistically significant associations were seen between circulating IL-6 and SAA (pre-treatment comparison: p=0.44, p<0.002; reduction by day 3 comparison: p=0.48, p<0.002). The strongest associations observed were between CRP and SAA (pre-treatment comparison: p=0.73, p<0.002; reduction by day 3: p=0.76, p<0.002). The results clearly show that TNFα blockade in the short term leads to normalisation of SAA levels in many patients.

Although the rapid response elements, CRP and SAA, are normally measured as markers of disease activity, rather than as pathophysiological agents in their own right, acute phase proteins may directly contribute to disease outcomes in RA. Prolonged, high level elevation in circulating SAA is associated with the development of secondary amyloidosis, a cause of renal failure and premature death in a small proportion of RA patients.

Equivalents

Those skilled in the art will know, or be able to ascertain, using no more than routine experimentation, many equivalents to the specific embodiments of the invention described herein. These and all other equivalents are intended to be encompassed by the following claims.

What is claimed is:

1. A method of treating a thrombotic disorder in an individual in need thereof comprising administering a therapeutically effective amount of an anti-human tumor necrosis factor-α monoclonal antibody or antigen-binding fragment thereof to the individual, wherein the thrombotic disorder is deep vein thrombosis.

* * * * *